United States Patent [19]
Wehrli

[11] Patent Number: 5,911,724
[45] Date of Patent: Jun. 15, 1999

[54] INSTRUMENT FOR ADJUSTMENT OSTEOTOMY OF A LOWER EXTREMITY

[75] Inventor: Ulrich Wehrli, Wabern, Switzerland

[73] Assignee: Mathys Medizinaltechnik AG, Bettlach, Switzerland

[21] Appl. No.: 08/894,826

[22] PCT Filed: May 21, 1996

[86] PCT No.: PCT/CH96/00195

§ 371 Date: Aug. 29, 1997

§ 102(e) Date: Aug. 29, 1997

[87] PCT Pub. No.: WO96/37154

PCT Pub. Date: Nov. 28, 1996

[30] Foreign Application Priority Data

May 26, 1995 [CH] Switzerland ............................. 1556/95

[51] Int. Cl.⁶ .................................................... A61B 17/56
[52] U.S. Cl. ................................ 606/88; 606/87; 606/102
[58] Field of Search ................................. 606/88, 89, 87, 606/86, 102, 82

[56] References Cited

U.S. PATENT DOCUMENTS

| | | |
|---|---|---|
| 4,349,018 | 9/1982 | Chambers . |
| 4,627,425 | 12/1986 | Reese . |
| 4,952,213 | 8/1990 | Bowman et al. ........................ 606/79 |
| 5,342,367 | 8/1994 | Ferrante et al. ......................... 606/86 |
| 5,364,401 | 11/1994 | Ferrante et al. ......................... 606/84 |
| 5,376,093 | 12/1994 | Newman .................................. 606/88 |
| 5,601,565 | 2/1997 | Huebner .................................. 606/87 |

FOREIGN PATENT DOCUMENTS

| | | |
|---|---|---|
| 0 231 885 | 8/1987 | European Pat. Off. . |
| 2679126 | 1/1993 | France . |

*Primary Examiner*—Guy V. Tucker
*Attorney, Agent, or Firm*—Walter C. Farley

[57] ABSTRACT

An instrument for performing a correctional osteotomy of a lower extremity of a patient has a securing frame (1), fixation elements (7, 8) for attaching the frame to the skeleton of the lower extremity of the patient, and securing components (6, 9) adjustably holding the fixation elements on the frame. A saw guide (25) is mounted on said frame so as to be angularly adjustable relative to the frame. An angle-indicating scale plate (10) is adjustably attached to one of the securing components. A rotation axis pin (12) penetrates the scale plate and points toward a location on the skeleton for intersection of bone cuts to be made. An angle determining component (23) is pivotable about the rotation axis pin and carries the saw guide and two pointers (26, 27) aligned with each other and alignable with a projection of a mechanical loading axis of the extremity of the patient, whereby adjustment of the pointers directly causes adjustment of the saw guide.

8 Claims, 2 Drawing Sheets

INSTRUMENT FOR ADJUSTMENT OSTEOTOMY OF A LOWER EXTREMITY

This application is filed under 35 USC 371 based on PCT/CH96/00195 filed on May 21, 1996.

FIELD OF THE INVENTION

This invention relates to instruments for the support of an orthopedic surgical operation for correction of the mechanical loading circumstances at the knee wherein a frame is attachable to the skeleton by two fixation elements with a saw guide angularly adjustable relative to the frame.

BACKGROUND OF THE INVENTION

The specific correction of the mechanical loading circumstances at the knee in a case of one-sided degenerated illness is a known and often applied method to regain freedom from pain and to enhance mobility without providing a prosthesis. In an orthopedic surgical operation, the position of the axis of the lower extremity is altered so that a relief of stress on the affected joint segment is achieved. The most commonly applied variant of this operation is the lateral set-on valgusating tibia-head-osteotomy when there is an existing impairment of the medial joint portion. In this procedure, an alteration of the axis of the leg toward knock knees is produced through removal of a wedge-shaped bone chip producing release of the ill medial joint compartment. Conditions for the clinical success of the adjustment osteotomy are, apart from the correct indication position, the exact determination of the correcting angle, the removal of a wedge-shaped bone chip corresponding to the correction angle, the quality of the areas of osteotomy and the stable micro-motion-free osteosynthesis by means of a suitable osteosynthesis implant.

In the case of a medial gonarthrosis, the mechanical axis that forms a straight line through the joint centers of the hip, knee and ankle joints in a healthy knee is displaced through the rearrangement by 20 to 30 mm toward the lateral joint part. The correction angle is the sum of the existing false position and an over-correction of the mechanical axis. Because of that over-correction, the load on the ill joint half is reduced and the opposite, healthy half is loaded a little more strongly. The bone wedge which is to be removed can either be removed horizontally, i.e., perpendicular to the axis of the diaphysis, or at an angle to it. When using the mentioned instruments, we choose an osteotomy course which is inclined rising toward the ill side to determine the rotating point of the osteotomy in the compact subchondral bone a few millimeters from the lateral limiting corticalis. The bone bridge so attained produces a tension boom and allows the simple osteosynthesis of the osteotomy by means of a reciprocal attached implant. For the production of this bone bridge, which is important for stability, the final choice of the general osteotomy angle relative to the joint axis is important since the crossing point of the wedge-shaped osteotomy in the compact bone volume directly below the joint provides good conditions for undisturbed healing without secondary correction loss.

For planning the operation, one uses an x-ray photograph of the full length of the extremity, centered on the joint, with the plane of the photograph corresponding with the frontal plane as exactly as possible to avoid projection errors. When taking measurements from the x-ray photograph, the factor of enlargement must be considered. Because x-ray photographs are affected by a nonlinear enlargement factor going out from the center of the ray, and the plane of the photography lies as a rule not exactly in the axis of the body because of position inaccuracies, this planning is always affected with faults. With patients of advanced age, the photography technique is often especially difficult. With given contraction of flexion, minor differences of rotation from the frontal plane have such consequences that the accuracy which is necessary to reach an optimal result is not given in planning. For conversion of the correction angle from the planning to determination of the guidance of the sawing tool angle, it is customary to use instruments which are attached to the skeleton and are provided with arrangements for guidance of a mechanically driven saw blade.

The authors of EP application 0 231 885 suggest the attachment of an instrument shaped as a circular arc and scaled in angular degrees by means of two pins which are positioned above and below the osteotomy in the tibia. The pins are positioned relative to each other along lines representing the wedge angle of the osteotomy. These pins carry a plate which forms the guide for the saw when positioned against the bone. With this, the angle and the plane of the wedge-shaped converging osteotomy planes are determined. Not determined is the location of the coincidence of the saw cuts at the peak of the bone wedge which is to be removed. This should, in the ideal case, be set some millimeters before the opposite cortical shell in the compact joint close spongiosa of the tibia so that, on one side, the osteotomy areas are apt to fit over the whole cross-section of the bone and on the other side, a minimal bone volume connected with shortening of the leg is removed, as little as is possible. Preservation of a thin deformable bone bridge is desired and ensures certain allocation of the osteotomy segments and increases the stability of the subsequent osteosynthesis in the sense of a tension boom. With the instrument suggested in EP 0 231 885, this crossing location is to be determined from the x-ray photograph and the instrument must be installed during the operation at the tibia with distance and orientation according to the planning. In this realization, the location of the cut edge is the central point of the angle-determining circular arc segment of the instrument.

In French patent application 2,679,126, a similar arrangement is described which is likewise attached to the skeleton by pins and allows osteotomies which permit the removal of a bone wedge sequently with a saw guide including a guide rail in the shape of a circular arc segment which exactly guides the saw, the saw being a reciprocating bone saw pivotable in angular degrees. In this device, the crossing location of the saw cuts must be planned on an x-ray photograph and transferred to the situation during the operation.

As described above, planning using an x-ray photograph contains some inevitable inaccuracies. In addition, it is to be expected that, when positioning one of the above described instruments on the patient, further inaccuracies will appear as to the location of the osteotomy wedge, particularly as the result of the fact that the positioning is not directly examinable in advance.

SUMMARY OF THE INVENTION

An object of the invention is to provide an instrument which allows one to perform adjusting wedge-shaped osteotomies on a lower extremity with high accuracy in which the result is independent of inaccuracies associated with planning using x-ray photographs. Additionally, the paths of the bone cuts, and particularly their intersection or crossing location, is to be exactly determinable and examinable before their execution.

An instrument in accordance with the invention has a securing frame enclosing the extremity which is attached to the skeleton of the patient surrounding the bone areas to be cut and which is a reference for the angle determining part. For fixating the securing frame, the subsequent anchorage of the implant used for the osteosynthesis and one or more pins to be bored into the bone are used. The securing frame forms the basis for a system of coordinates for the position and the correction angle of the correction osteotomy. On the angle determining part is guided the saw guide and a pointer system connected with it and representing the projection of the mechanical proportion of the axis. Alteration of the mechanical axis indicated by pivoting the pointers is consequently directly transferred to the saw guide. The rotation axis of the angle determining part corresponds to the crossing location of the bone cuts executed along the saw guide. By means of the guide and clamping devices, the rotation axis is freely selectable and is directly indicated at the skeleton. Thus, all of the variables determining the operation are adjustable directly at the skeleton and are examinable, and are therefore independent of planning, affected by mistakes on the basis of x-ray photographs.

BRIEF DESCRIPTION OF THE DRAWINGS

An embodiment of the invention for a valgusated tibia-correction-osteotomy is described in the following with reference to the accompanying drawings, wherein.

DETAILED DESCRIPTION OF A PREFERRED EMBODIMENT

Figure 1:
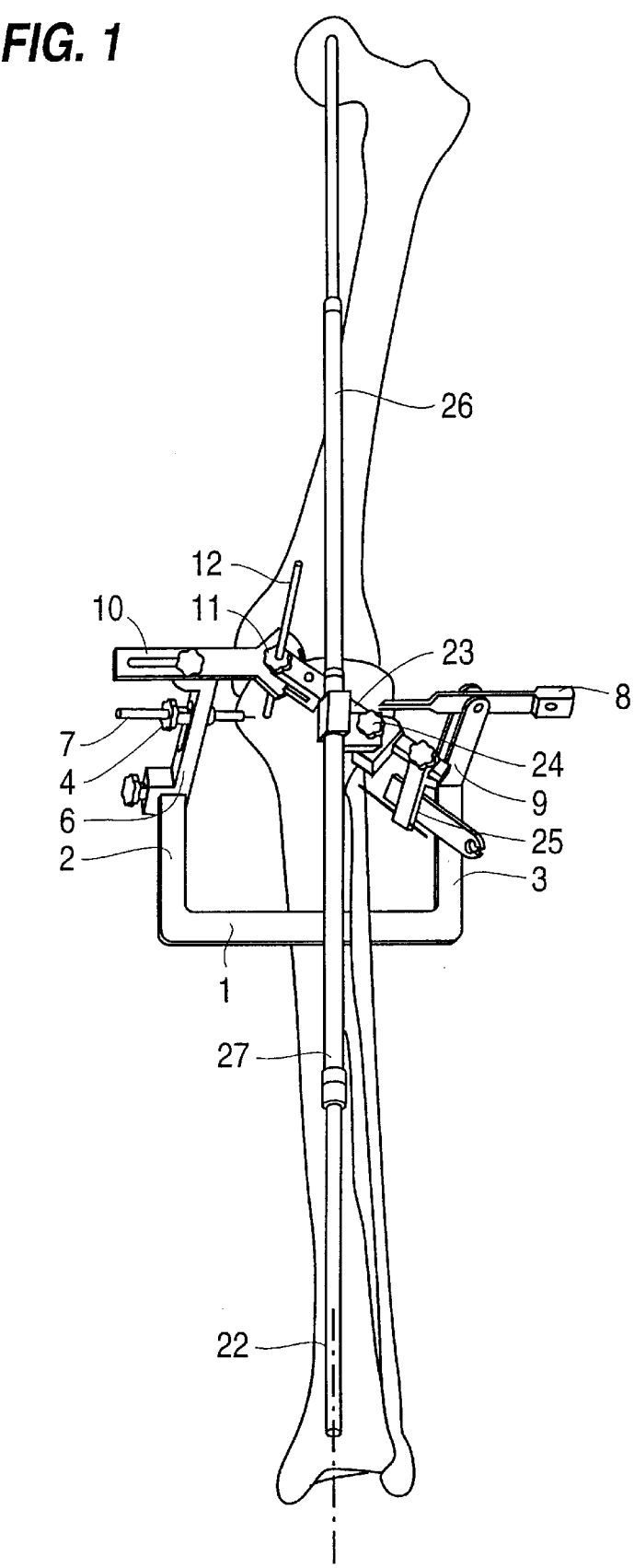
FIG. 1 is a schematic front elevation of a skeletal lower extremity of a patient with an instrument according to the invention positioned thereon.
Figure 2:
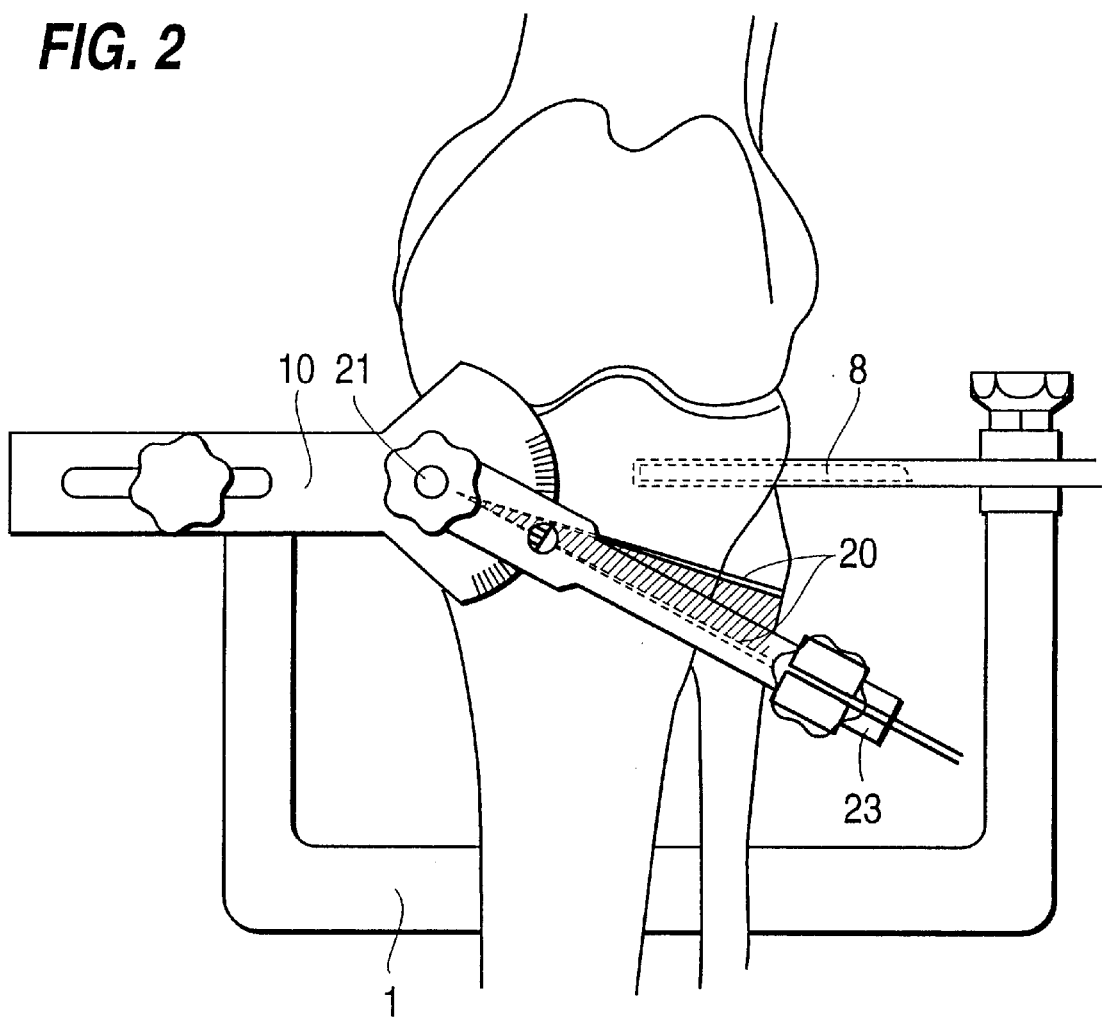
FIG. 2 is an enlarged partial schematic diagram of a portion of the apparatus of FIG. 1 showing wedge-shaped saw cuts of the correction osteotomy with a predetermined crossing location of the cuts.

A securing frame 1 is fixed to the skeleton on both sides below the knee. Parallel legs 2 and 3 of the securing frame are connected respectively by a pin guide 6 and a securing clamp 9 at least one of which is attached so that it is pivotable about an axis or moveable in a plane. In the example shown, clamp 9 is pivotably attached and is clampable around the axis of leg 3 of the securing frame. About 6 to 10 mm below the joint plane, a pin 7 guided in pin guide 6 is inserted parallel to the joint plane from the medial into the bone so that the position of the pin is adjustable along the pin guide and perpendicular to it by a clamp guide 4.

A bone chisel 8 which is held in clamp 9 and driven into the bone forms the lateral attachment. In order to use the instrument at the left rather than the right extremity, the clamping of bone chisel 8 and the guide rail for pin guide 6 are mounted in a position reversed 180° from that shown. The two attachment elements, pin 7 and bone chisel 8, are adjustable in height so that the securing frame is positionable relative to the skeleton. Bone chisel 8 may additionally serve for fixation of the instrument for preparation of the bone bearing for the subsequent osteosynthesis implant, for example, a bent half-tube plate. On pin guide 6, an angle determining part 10 is movably attached so that the center of rotation 11 of the angle determining part represents a crossing point 21 of bone cuts 20. This point is indicated by a lowerable pin 12 penetrating part 10 and pointing directly at the skeleton.

The general angle of the wedge-shaped osteotomy to the tibial axis may be chosen freely through the initial angle of a pivoting arm 23. On the pivoting arm, which is shaped as a longitudinal guide, a saw guide 25 and a pointer holding device 24, which is pivotable and clampable in itself, is guided.

Small medial and enlarged lateral incisions are made and the instrument is then attached to the skeleton, after which the crossing point of the saw cuts is set by moving angle determining part 10. After the choice of the general angle of the osteotomy is made, the pair of pointers comprising hip side pointer 26 and tibia side pointer 27 is positioned above the center of the knee, adjusted parallel with the tibial axis 22 and clamped relative to pivoting arm 23 by means of pointer holding device 24. The angular position of the pivoting arm may be read on the angle scale and can be determined from the clamping screw at the rotation axis. For execution of the first saw cut, saw guide 25 is pushed against the bone, clamped at the pivoting arm and secured in this position by a pin which is positioned in the bone by a corresponding borehole in the saw guide.

After previous osteotomy of the fibula, the first saw cut of the wedge-shaped osteotomy is made. The pin locking of the saw guide is loosened and the correction of the leg axis is adjusted through the pointer pointing toward the hip joint. The spina iliaca anterior-superior, which is easy to identify during the operation and is situated 2–3 cm lateral of the center of the hip joint, serves as a reference. For achievement of the desired over-correction, hip pointer 26 is adjusted to a point 4.5 to 7 centimeters medial of the spina. This adjustment method, having reference points lying far apart, offers the advantage of small errors. The easily meetable measuring tolerance of one centimeter by the adjustment of the pointers relative to the spina produces a maximum angular error of approximately 1 to 1.5°. The accuracy which is necessary for an optimal result of the operation is 2 to 3°, which is far larger than the maximum anticipated error achievable with an instrument according to the invention.

By adjustment of hip pointer 26, pivoting arm 23 of the instrument and therewith saw guide 25 are automatically likewise rotated to the correction angle. For controlling, the chosen correction angle may be read directly on a scale at angle determining part 10. From the pointers, which represent the mechanical axes of the leg, the correction may be effected directly related to the axes. The correction angle results therefrom and may be read, although knowledge of this angle is not necessary for completion of the operation. After the chosen correction has been set, the saw guide is fixed again in the new position by the pin which passes through the borehole of the saw guide, and the second saw cut is made. After removal of the bone wedge, the instrument is removed from the skeleton and the osteotomy areas are closed toward each other. The adapted osteosynthesis implant, a bent half-tube plate, is anchored in a bearing prepared by bone chisel 8 and screwed down against the tibia. Alternatively, other implants may be used, for instance bone clamps.

I claim:

1. An instrument for performing an adjustment osteotomy of a lower extremity of a patient comprising a securing frame (1);

first and second fixation elements (7, 8) for attaching said frame to the skeleton of a lower extremity of a patient;

first and second securing components (6, 9) adjustably holding said first and second fixation elements, respectively, on said frame;

a saw guide (25) mounted on said frame, said saw guide being adjustable to a plurality of angles relative to said frame;

an angle-indicating scale plate (10) adjustably attached to one of said securing components;

a rotation axis pin (12) penetrating said scale plate for pointing toward a location on said skeleton for intersection of bone cuts to be made therein; and an angle determining component (23) pivotable about said rotation axis pin and carrying said saw guide and two pointers (26, 27) aligned with each other and alignable with a projection of a mechanical loading axis of the extremity of the patient, whereby adjustment of said pointers directly causes adjustment of said saw guide.

2. An instrument according to claim 1 wherein said frame is generally C-shaped comprising two parallel legs, one of said securing components being attached to each of said parallel legs.

3. An instrument according to claim 2 wherein at least one of said securing components (6, 9) is adjustable relative to said parallel leg.

4. An instrument according to claim 1 wherein said first fixation element comprises a pin (7), said first securing component (6) comprises a pin guide with a guide clamp holding said pin so that the height of said pin relative to said frame is adjustable.

5. An instrument according to claim 4 wherein said second fixation element comprises a bone chisel (8) and said second securing component (9) comprises a chisel clamp holding said chisel, said chisel clamp being pivotable relative to said frame.

6. An instrument according to claim 1 including a fastening element (24) connecting said two pointers (26, 27) to said saw guide, said fastening element permitting angular adjustment of said pointers relative to said saw guide.

7. An instrument according to claim 1 wherein the length of each of said two pointers (26, 27) is adjustable.

8. An instrument according to claim 7 wherein each of said two pointers comprises telescoping sections permitting said length to be adjustable.

* * * * *